United States Patent
Kataoka et al.

(10) Patent No.: US 12,126,368 B2
(45) Date of Patent: Oct. 22, 2024

(54) NON-TRANSITORY COMPUTER-READABLE STORAGE MEDIUM FOR STORING INFORMATION PROCESSING PROGRAM, INFORMATION PROCESSING METHOD, AND INFORMATION PROCESSING DEVICE

(71) Applicant: FUJITSU LIMITED, Kawasaki (JP)

(72) Inventors: Masahiro Kataoka, Kamakura (JP); Hiromi Koga, Fukuoka (JP); Mariko Taga, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 211 days.

(21) Appl. No.: 17/984,396

(22) Filed: Nov. 10, 2022

(65) Prior Publication Data

US 2023/0066586 A1 Mar. 2, 2023

Related U.S. Application Data

(63) Continuation of application No. PCT/JP2020/022368, filed on Jun. 5, 2020.

(51) Int. Cl.
*H03M 7/00* (2006.01)
*G06F 18/22* (2023.01)
(Continued)

(52) U.S. Cl.
CPC .......... *H03M 7/3082* (2013.01); *G06F 18/22* (2023.01); *G16C 20/30* (2019.02); *G16C 20/50* (2019.02)

(58) Field of Classification Search
CPC ....... H03M 7/3082; G16C 20/50; G06F 18/22
(Continued)

(56) References Cited

U.S. PATENT DOCUMENTS 5,254,990 A * 10/1993 Yoshida .............. H03M 7/3088
341/51
6,373,411 B1 * 4/2002 Shoham .................. H03M 7/42
341/50
(Continued)

FOREIGN PATENT DOCUMENTS

JP H11-306188 A 11/1999
JP 2018-147374 A 9/2018
(Continued)

OTHER PUBLICATIONS

Extended European Search Report dated Jun. 21, 2023 for corresponding European Patent Application No. 20939180.4, 8 pages.
(Continued)

*Primary Examiner* — Peguy Jean Pierre
(74) *Attorney, Agent, or Firm* — Fujitsu Intellectual Property Center

(57) ABSTRACT

A computer-readable storage medium storing a program for causing a computer to perform processing including: dividing a sequence indicating a rational formula of a compound, into a character string of a minimum unit of the sequence and a branch symbol indicating a branched portion of the compound; generating a first coded sequence by using a group dictionary indicating a relationship between the sequence and the compression code, the generating including assigning a compression code to the character string of the minimum unit, and assigning the compression code according to a type of the branched portion to the branch symbol; and generating a second coded sequence by using a primary structure dictionary indicating a relationship between a group primary structure of the sequence and the compression code, the generating of the second coded sequence including encoding the compression code in the first coded sequence in units of the group primary structure.

15 Claims, 21 Drawing Sheets

(51) Int. Cl.
*G16C 20/30* (2019.01)
*G16C 20/50* (2019.01)
*H03M 7/30* (2006.01)

(58) Field of Classification Search
USPC .......................................................... 343/50
See application file for complete search history.

(56) References Cited

U.S. PATENT DOCUMENTS

| | | | |
|---|---|---|---|
| 7,064,684 B2 * | 6/2006 | Lablans | H04B 1/707 |
| | | | 341/50 |
| 2010/0099891 A1 | 4/2010 | Okuno et al. | |
| 2012/0109972 A1 | 5/2012 | Boyer et al. | |
| 2013/0124152 A1 | 5/2013 | Cho | |
| 2018/0143954 A1 | 5/2018 | Nakamura et al. | |

FOREIGN PATENT DOCUMENTS

| | | |
|---|---|---|
| JP | 2019-204362 A | 11/2019 |
| WO | 2007/139037 A1 | 12/2007 |
| WO | 2017/017738 A1 | 2/2017 |

OTHER PUBLICATIONS

Melville, James L. et al., "Similarity by Compression", Journal of Chemical Information and Modeling, vol. 47, No. 1, Dec. 9, 2006, pp. 25-33, XP093052804, US, ISSN: 1549-9596, DOI: 10.1021/ci600384z.

Karthikeyan, M. et al., "Encoding and Decoding Graphical Chemical Structures as Two-Dimensional (PDF417) Barcodes", Journal of Chemical Information and Computer Sciences, American Chemical Society Colombus, Ohio, US, vol. 45, No. 3, May 1, 2005, pp. 572-580, XP002765180, ISSN: 0095-2338.

Cai, Chaoqian et al., "Molecular Similarity: Methods and Performance", Chinese Journal of Chemistry, Zhongguo Kexueyuan, Cn, vol. 31, No. 9, Sep. 16, 2013, pp. 1123-1132, XP071929110, ISSN: 1001-604X, DOI: 10.1002/cjoc.201300390.

Willett, Peter, "Chemical Similarity Searching", Journal of Chemical Information and Computer Sciences, American Chemical Society, Colombus, Ohio, US, vol. 38, No. 6, Nov. 1, 1998, pp. 983-996, XP000890390, ISSN: 0095-2338, DOI: 10.1021/ci9800211.

Valentin Khrulkov et al., "Hyperbolic Image Embeddings", Cornell University, arXiv: 1904.02239v1 [cs.CV], pp. 1-10, Apr. 3, 2019 (Total 10 pages).

International Search Report and Written Opinion of the International Searching Authority (Form PCT/ISA/210, 220, and 237), mailed in connection with PCT/JP2020/022368 and mailed Sep. 24, 2020 (Total 10 pages).

* cited by examiner

FIG. 5

| COMPOUND IDENTIFICATION INFORMATION | RATIONAL FORMULA |
|---|---|
| C101 | INFORMATION OF SYMBOL SEQUENCE INDICATING RATIONAL FORMULA OF COMPOUND IDENTIFICATION INFORMATION "C101" |
| C102 | INFORMATION OF SYMBOL SEQUENCE INDICATING RATIONAL FORMULA OF COMPOUND IDENTIFICATION INFORMATION "C102" |
| C103 | INFORMATION OF SYMBOL SEQUENCE INDICATING RATIONAL FORMULA OF COMPOUND IDENTIFICATION INFORMATION "C103" |
| ... | ... |

FIG. 6

| BRANCH SYMBOL | COMPRESSION CODE |
|---|---|
| ( | 30h |
| ) | 31h |
| $)_2$ | 32h |
| $)_3$ | 33h |

FIG. 7

| COMPRESSION CODE | GROUPING | NAME EXAMPLE | RATIONAL FORMULA |
|---|---|---|---|
| 8000h | METHYL GROUP | METHANE | CH3 |
| 8001h | ETHYL GROUP | ETHANE | CH3CH2 |
| 8002h | PROPYL GROUP | PROPANE | CH3CH2CH2 |
| 8003h | BUTYL GROUP | BUTANE | CH3CH2CH2CH2 |
| ... | ... | ... | ... |
| 8013h | NITRO GROUP | NITRO ··· | NO2 |
| ... | ... | ... | ... |
| 805Ah | HYDROXY GROUP | ····-OL | OH |
| 805Bh | ALDEHYDE GROUP | ····-ALDEHYDE | OHO |
| ... | ... | ... | ... |

| COMPRESSION CODE | GROUPING | NAME EXAMPLE | CO-OCCURRENCE RATE OF GROUP 140d | | | | | | |
|---|---|---|---|---|---|---|---|---|---|
| | | | GROUP (COMPRESSION CODE) | CO-OCCURRENCE RATE | GROUP (COMPRESSION CODE) | CO-OCCURRENCE RATE | GROUP (COMPRESSION CODE) | CO-OCCURRENCE RATE | |
| 8000h | METHYL GROUP | METHANE | 8028h | 78% | 8132h | 63% | 80F5h | 33% | ... |
| 8001h | ETHYL GROUP | ETHANE | 81E3h | 81% | 8021h | 71% | 8241h | 20% | ... |
| 8002h | PROPYL GROUP | PROPANE | | | | | | | |
| 8003h | BUTYL GROUP | BUTANE | | | | | | | |
| ... | ... | ... | | | | | | | |
| 8013h | NITRO GROUP | NITRO... | | | | | | | |
| ... | ... | ...-OL | | | | | | | |
| 805Ah | HYDROXY GROUP | ....-ALDEHYDE | | | | | | | |
| 805Bh | ALDEHYDE GROUP | ... | | | | | | | |
| ... | ... | | | | | | | | |

FIG. 9

| COMPOUND IDENTIFICATION INFORMATION | COMPRESSION CODE SEQUENCE |
|---|---|
| C101 | COMPRESSION CODE SEQUENCE OBTAINED BY ENCODING RATIONAL FORMULA OF COMPOUND IDENTIFICATION INFORMATION "C101" |
| C102 | COMPRESSION CODE SEQUENCE OBTAINED BY ENCODING RATIONAL FORMULA OF COMPOUND IDENTIFICATION INFORMATION "C102" |
| C103 | COMPRESSION CODE SEQUENCE OBTAINED BY ENCODING RATIONAL FORMULA OF COMPOUND IDENTIFICATION INFORMATION "C103" |
| ... | ... |

FIG. 11

| COMPRESSION CODE | GROUPING | NAME | COMPRESSION CODE SEQUENCE |
|---|---|---|---|
| F00000h | G1 | α PRIMARY STRUCTURE | 02h8028h······03h |
| F00001h | G1 | β PRIMARY STRUCTURE | 02h80F5h····03h |
| F00002h | G1 | γ PRIMARY STRUCTURE | 02h81E3h········03h |
| F00003h | G1 | δ PRIMARY STRUCTURE | ····· |
| ... | ... | ... | ····· |

| COMPRESSION CODE | GROUPING | NAME | CO-OCCURRENCE RATE OF GROUP PRIMARY STRUCTURE 140h | | | | | | |
|---|---|---|---|---|---|---|---|---|---|
| | | | GROUP PRIMARY STRUCTURE (COMPRESSION CODE) | CO-OCCURRENCE RATE | GROUP PRIMARY STRUCTURE (COMPRESSION CODE) | CO-OCCURRENCE RATE | GROUP PRIMARY STRUCTURE (COMPRESSION CODE) | CO-OCCURRENCE RATE | |
| F00000h | G1 | α PRIMARY STRUCTURE | F00011h | 78% | F00101h | 63% | F00225h | 51% | ... |
| F00001h | G1 | β PRIMARY STRUCTURE | F00645h | 81% | F00108h | 71% | F00555h | 57% | ... |
| F00002h | G1 | γ PRIMARY STRUCTURE | | | | | | | |
| F00003h | G1 | δ PRIMARY STRUCTURE | | | ... | | | | |
| ... | ... | ... | | | | | | | |

FIG. 13

| COMPOUND IDENTIFICATION INFORMATION | COMPRESSION CODE SEQUENCE OF GROUP PRIMARY STRUCTURE | | | | |
|---|---|---|---|---|---|
| C101 | F00112h | F00332h | F00110h | F00460h | ... |
| C102 | F00232h | F00582h | F00874h | F00209h | ... |
| C103 | F00102h | F00082h | F00874h | F00009h | ... |
| ... | ... | | | | |

FIG. 15

| PROPERTY NUMBER | COMPRESSION CODE | NAME |
|---|---|---|
| I101 | 8000h | METHANE |
| | 8120h | ... |
| | 8234h | ... |
| I102 | 8004h | ETHANE |
| | 8005h | ... |
| | 8006h | ... |
| | 8007h | ... |
| ... | ... | ... |

| COMPRESSION CODE | VECTOR |
|---|---|
| 8000h | Vec1-1 |
| 8001h | Vec1-2 |
| 8002h | Vec1-3 |
| ... | ... |
| 8013h | Vec1-3 |
| ... | ... |
| 805Ah | Vec1-10 |
| 805Bh | Vec1-11 |
| ... | ... |

| COMPRESSION CODE | VECTOR |
|---|---|
| F00000h | Vec2-1 |
| F00001h | Vec2-2 |
| F00002h | Vec2-3 |
| F00003h | Vec2-4 |
| ... | ... |

| COMPOUND IDENTIFICATION INFORMATION | VECTOR (1) | VECTOR (2) | VECTOR (3) | ... |
|---|---|---|---|---|
| C101 | 0.28213 | 0.14975 | 0.18975 | ... |
| C102 | 0.97325 | 0.23800 | 0.15575 | ... |
| C103 | 0.309085 | 0.13800 | 0.14925 | ... |
| ... | ... | ... | ... | ... |

140n

NON-TRANSITORY COMPUTER-READABLE STORAGE MEDIUM FOR STORING INFORMATION PROCESSING PROGRAM, INFORMATION PROCESSING METHOD, AND INFORMATION PROCESSING DEVICE

CROSS-REFERENCE TO RELATED APPLICATION

This application is a continuation application of International Application PCT/JP2020/022368 filed on Jun. 5, 2020 and designated the U.S., the entire contents of which are incorporated herein by reference.

FIELD

The embodiment discussed herein is related to a non-transitory computer-readable storage medium storing an information processing program, and the like.

BACKGROUND

There are substances with a molecular weight of more than 1000, such as sugars including starch, cellulose, and the like, proteins, nucleic acids, and natural rubber, and such substances are also called high-molecular compounds.

Here, in a case of developing a new drug or a new material, it is required to search for already developed high-molecular compounds and evaluate similarity.

For example, there are the following existing techniques 1 and 2 as techniques for evaluating the similarity between compounds. The existing technique 1 is a system for searching for an amino acid sequence of a compound such as a protein, which is described by amino acid symbols, using an input character string. Furthermore, in the existing technique 2, a vector is assigned to a descriptive expression such as counting the number of functional groups and atom types of a compound, and the similarity is evaluated with respect to the vector pre-assigned to each compound.

Examples of the related art include [Patent Document 1] Japanese Laid-open Patent Publication No. 11-306188; [Patent Document 2] International Publication Pamphlet No. WO 2007/139037; and [Patent Document 3] Japanese Laid-open Patent Publication No. 2019-204362.

SUMMARY

According to an aspect of the embodiments, there is provided a non-transitory computer-readable storage medium storing an information processing program for causing a computer to perform processing including: dividing a sequence that indicates a rational formula of a compound, into a character string of a minimum unit of the sequence and a branch symbol that indicates a branched portion of the compound; generating a first coded sequence by using a group dictionary that indicates a relationship between the sequence of the rational formula of the compound and the compression code, the generating of the first coded sequence including assigning, based on the group dictionary, a compression code to the character string of the minimum unit, and assigning, based on the group dictionary, the compression code according to a type of the branched portion to the branch symbol; and generating a second coded sequence by using a group primary structure dictionary that indicates a relationship between a group primary structure of the sequence of the rational formula of the compound and the compression code, the generating of the second coded sequence including encoding, based on the group primary structure dictionary, the compression code included in the first coded sequence in units of the group primary structure.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 5 is a table illustrating an example of a data structure of a chemical structural formula file.

FIG. 6 is a table illustrating an example of a data structure of a branch code table.

FIG. 7 is a table illustrating an example of a data structure of a group dictionary.

FIG. 8 is a table illustrating an example of a data structure of a group HMM.

FIG. 9 is a table illustrating an example of a data structure of a chemical structural formula compressed file.

FIG. 11 is a table illustrating an example of a data structure of a group primary structure dictionary.

FIG. 12 is a table illustrating an example of a data structure of a group primary structure HMM.

FIG. 13 is a table illustrating an example of a data structure of a group primary structure compressed file.

FIG. 15 is a table illustrating an example of a data structure of a property management table.

FIG. 16A is a table illustrating an example of a data structure of a group vector table.

FIG. 16B is a table illustrating an example of a data structure of a group primary structure vector table.

FIG. 16C is a table illustrating an example of a data structure of a transition table.

DESCRIPTION OF EMBODIMENTS

However, the above-described existing techniques have a problem that the accuracy of similarity evaluation of high-molecular compounds is low.

In one aspect, an object of the present invention is to provide an information processing program, an information processing method, and an information processing device capable of improving evaluation of accuracy of similarity evaluation of high-molecular compounds.

Hereinafter, an embodiment of an information processing program, an information processing method, and an information processing device disclosed in the present application will be described in detail with reference to the drawings. Note that the present embodiment does not limit the present disclosure.

Embodiment

Figure 1:
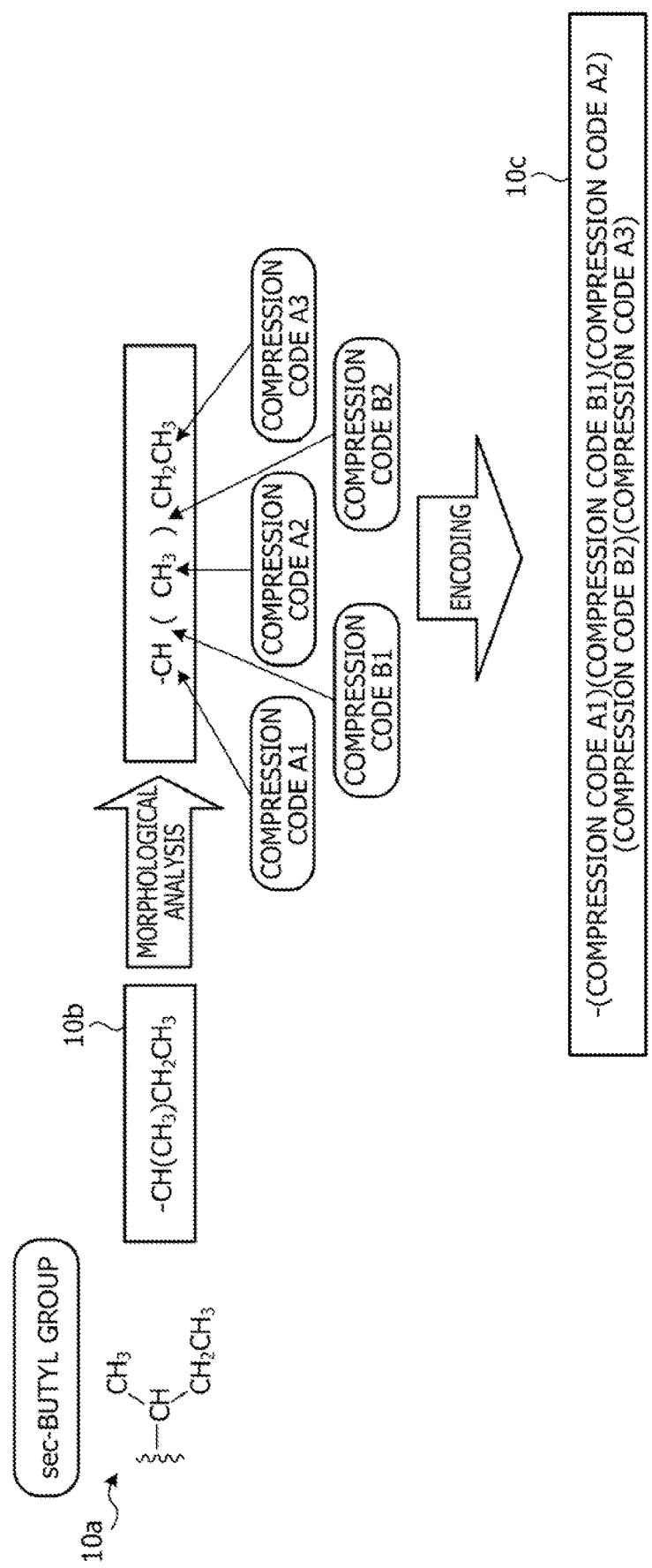
FIG. 1 is a diagram (1) for describing processing in which an information processing device according to the present embodiment encodes a compound.

FIG. 1 is a diagram (1) for describing processing in which an information processing device according to the present embodiment encodes a compound. Here, a case of encoding a compound will be described, but encoding can be similarly performed in a case of encoding a high-molecular compound. In FIG. 1, a case where a sec-butyl group contained in a certain compound can be further decomposed into a methyl group and an ethyl group, and the methyl group and the ethyl group are encoded will be described. A chemical structural formula 10a of the sec-butyl group branches from "CH" into a methyl group "$CH_3$" and an ethyl group "$CH_2CH_3$". A rational formula 10b of the chemical structural formula 10a of the sec-butyl group is represented by a sequence such as "—$CH(CH_3) \ CH_2CH_3$".

The information processing device divides the sequence included in the rational formula 10b into a character string of a minimum unit (meaningful unit) of the sequence and a symbol representing a branched portion of the compound by executing a morphological analysis for the rational formula 10b. In the following description, the character string of the minimum unit of the sequence, which is also a code of a meaningful unit, is referred to as a "unit character string", and the symbol representing a branched portion of the compound is referred to as a "branch symbol".

In the example illustrated in FIG. 1, the information processing device divides the rational formula 10b into "CH", "(", "$CH_3$", ")", and "$CH_2CH_3$". "CH", "$CH_3$", and "$CH_2CH_3$" are unit character strings of groups (or functional groups). "(" and ")" are branch symbols.

The information processing device assigns a compression code to each unit character string on the basis of a group dictionary indicating a relationship between the unit character string of the sequence of the rational formula of the compound and the compression code. For example, the information processing device assigns a compression code A1, a compression code A2, and a compression code A3 to "CH", "$CH_3$", and "$CH_2CH_3$", respectively.

The information processing device assigns a compression code to each branch symbol on the basis of a branch code table indicating a relationship between the branch symbol and the compression code. For example, the information processing device assigns a compression code B1 and a compression code B2 to "(" and ")".

The information processing device generates a compression code sequence 10c obtained by encoding the rational formula 10b by executing the above-described processing. The information processing device encodes the compound by executing the above-described processing for a remaining portion of the compound (not illustrated). Furthermore, the information processing device generates group vectors by collecting similar groups such as the butyl group and the sec-butyl group, and collectively embedding the groups in a Poincare space.

The information processing device further encodes the compression code sequence 10c in units of a group primary structure, focusing on branches. The information processing device calculates a vector of the group primary structure of the compound by adding the vectors of the plurality of groups constituting the group primary structure.

Figure 2:
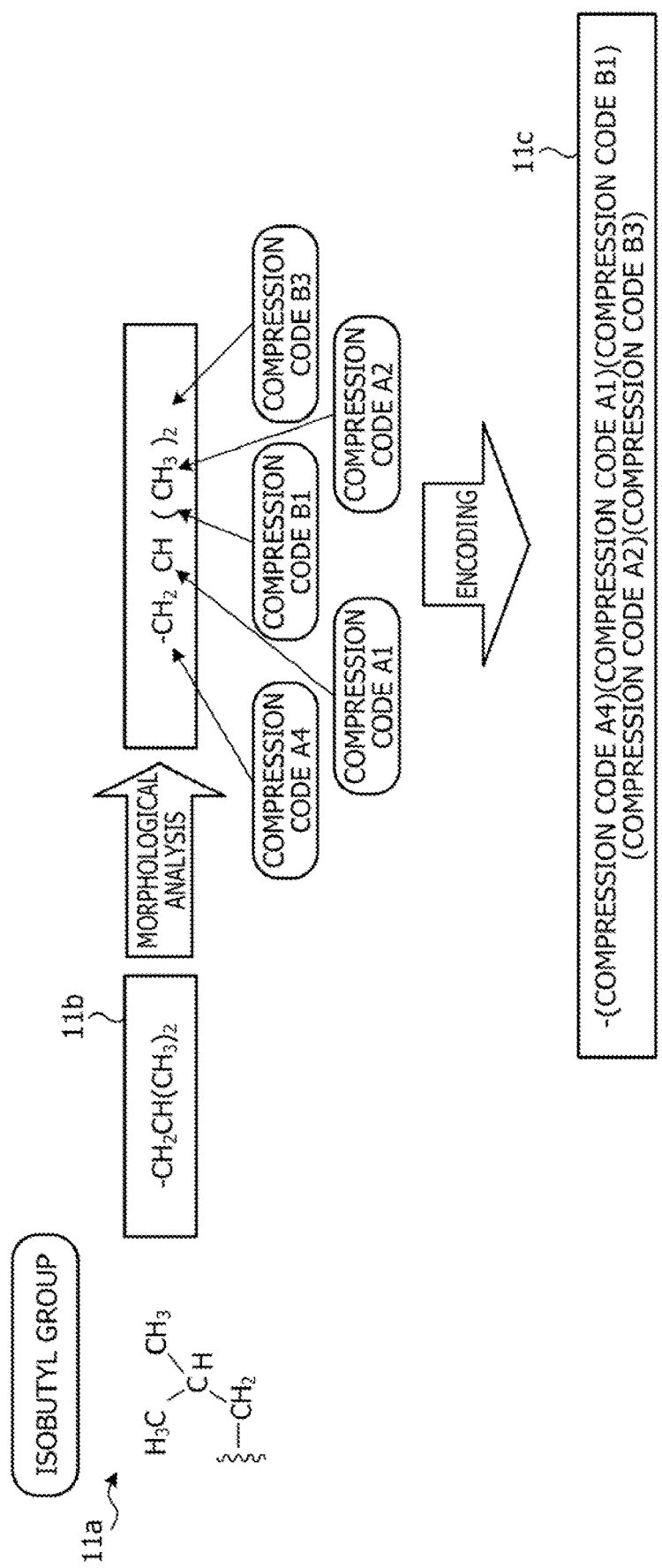
FIG. 2 is a diagram (2) for describing processing in which the information processing device according to the present embodiment encodes a compound.

FIG. 2 is a diagram (2) for describing processing in which the information processing device according to the present embodiment encodes a compound. In FIG. 2, a case of encoding an isobutyl group contained in a certain compound will be described. A chemical structural formula 11a of the isobutyl group branches from "CH" to "$CH_2$" and two pieces of "$CH_3$". A rational formula 11b of the chemical structural formula 11a of the isobutyl group is represented by a sequence such as "—$CH_2CH(CH_3)_2$".

The information processing device divides the sequence included in the rational formula 11b into a unit character string and a branch symbol by executing a morphological analysis for the rational formula 11b. In the example illustrated in FIG. 2, the information processing device divides the rational formula 11b into "$CH_2$", "CH", "(", "$CH_3$", and ")$_2$". "$CH_2$", "CH", and "$CH_3$" are unit character strings. "(" and ")$_2$" are branch symbols.

The information processing device assigns a compression code to each unit character string on the basis of a group dictionary indicating a relationship between the unit character string of the sequence of the rational formula of the compound and the compression code. For example, the information processing device assigns a compression code A4, the compression code A1, and the compression code A2 to "$CH_2$", "CH", and "$CH_3$", respectively.

The information processing device assigns a compression code to each branch symbol on the basis of a branch code table indicating a relationship between the branch symbol and the compression code. For example, the information processing device assigns the compression code B1 and a compression code B3 to "(" and ")$_2$".

The information processing device generates a compression code sequence 11c obtained by encoding the rational formula 11b by executing the above-described processing. The information processing device encodes the compound by executing the above-described processing for a remaining portion of the compound (not illustrated). Furthermore, the information processing device generates group vectors by collecting similar groups and collectively embedding the groups in a Poincare space.

The information processing device further encodes the compression code sequence 11c in units of a group primary structure. The information processing device calculates a vector of the primary structure of the compound by adding the vectors of the plurality of groups constituting the group primary structure.

Figure 3:
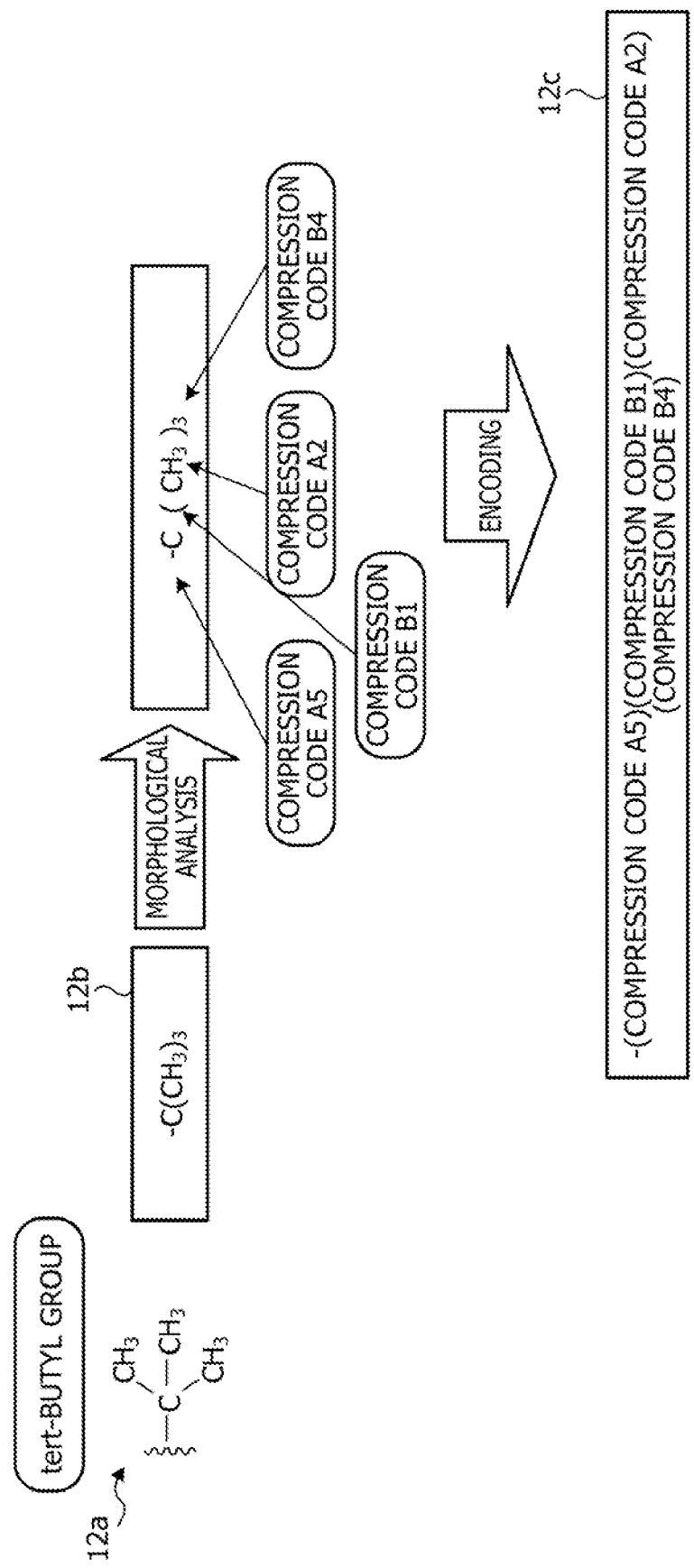
FIG. 3 is a diagram (3) for describing processing in which the information processing device according to the present embodiment encodes a compound.

FIG. 3 is a diagram (3) for describing processing in which the information processing device according to the present embodiment encodes a compound. In FIG. 3, a case of encoding a tert-butyl group contained in a certain compound will be described. A chemical structural formula 12a of the tert-butyl group branches from "C" to three pieces of "$CH_3$". A rational formula 12b of the chemical structural formula 12a of the tert-butyl group is represented by a sequence such as "—$C(CH_3)_3$".

The information processing device divides the sequence included in the rational formula 12b into a unit character string and a branch symbol by executing a morphological analysis for the rational formula 12b. In the example illustrated in FIG. 3, the information processing device divides the rational formula 12b into "C", "(", "$CH_3$", and ")$_3$". "$CH_2$", "C", and "$CH_3$" are unit character strings. "(" and ")$_3$" are branch symbols.

The information processing device assigns a compression code to each unit character string on the basis of a group dictionary indicating a relationship between the sequence of the rational formula of the compound and the compression code. For example, the information processing device assigns a compression code A5 and the compression code A2 to "C" and "$CH_3$", respectively.

The information processing device assigns a compression code to each branch symbol on the basis of a branch code table indicating a relationship between the branch symbol and the compression code. For example, the information processing device assigns the compression code B1 and a compression code B4 to "(" and ")$_3$".

The information processing device generates a compression code sequence 12c obtained by encoding the rational formula 12b by executing the above-described processing. The information processing device encodes the compound by executing the above-described processing for a remaining portion of the compound (not illustrated). Furthermore, the information processing device generates group vectors by collecting similar groups and collectively embedding the groups in a Poincare space.

The information processing device further encodes the compression code sequence 12c in units of a group primary structure. The information processing device calculates a vector of the primary structure of the compound by adding the vectors of the plurality of groups constituting the group primary structure.

As described above, the information processing device according to the present embodiment divides the sequence indicating the rational formula of the compound into the unit character strings and branch symbols, and encodes the rational formula of the compound on the basis of the group dictionary. Furthermore, the information processing device generates group vectors by collecting similar groups and collectively embedding the groups in a Poincare space. The information processing device further encodes the encoded rational formula of the compound in units of the group primary structure, and calculates the vector of the primary structure of the compound by adding the vectors of the plurality of groups constituting the primary structure. As a result, it is possible to calculate the groups of the compound and the vector of the group primary structure with accuracy, and the accuracy of similarity evaluation is improved by executing similarity evaluation of a high-molecular compound using the groups and the vector of the group primary structure. Note that the rational formula is an example of a chemical structural formula to be encoded. The rational formula may be a chemical structural formula expressed by SMILES notation or the like.

Figure 4:
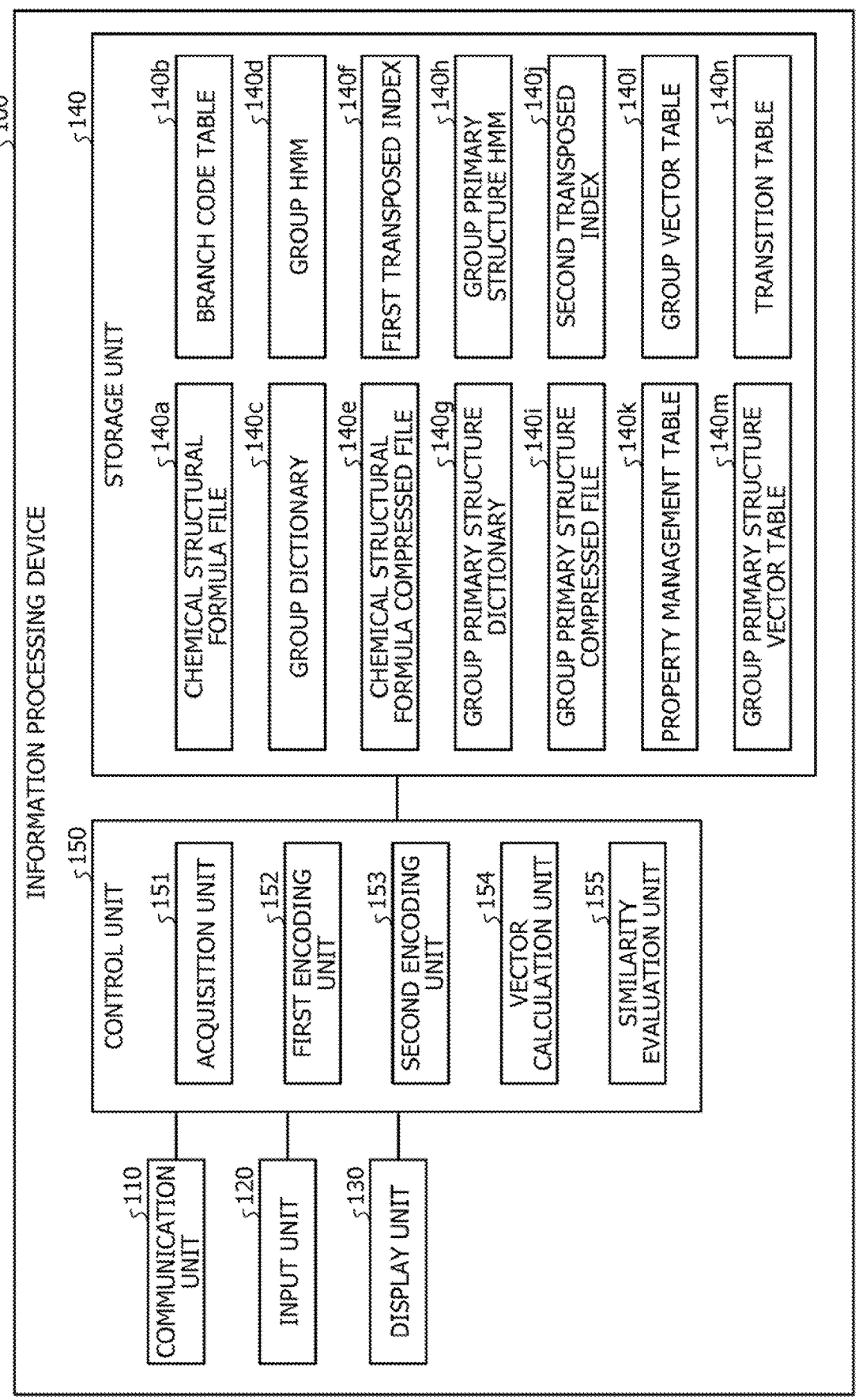
FIG. 4 is a functional block diagram illustrating a configuration of the information processing device according to the present embodiment.

Next, an example of a configuration of the information processing device according to the present embodiment will be described. FIG. 4 is a functional block diagram illustrating the configuration of the information 4, an information processing device 100 includes a communication unit 110, an input unit 120, a display unit 130, a storage unit 140, and a control unit 150.

The communication unit 110 is connected to an external device or the like by a wired or wireless means, and transmits and receives information to and from the external device or the like. For example, the communication unit 110 is implemented by a network interface card (NIC) or the like. The communication unit 110 may be connected to a network (not illustrated).

The input unit 120 is an input device that inputs various types of information to the information processing device 100. The input unit 120 corresponds to a keyboard, a mouse, a touch panel, or the like.

The display unit 130 is a display device that displays information output from the control unit 150. The display unit 130 corresponds to a liquid crystal display, an organic electro luminescence (EL) display, a touch panel, or the like.

The storage unit 140 has a chemical structural formula file 140a, a branch code table 140b, a group dictionary 140c, a group HMM 140d, a chemical structural formula compressed file 140e, and a first transposed index 140f. The storage unit 140 has a group primary structure dictionary 140g, a group primary structure HMM 140h, a group primary structure compressed file 140i, a second transposed index 140j, a property management table 140k, and a transition table 140n. The storage unit 140 is implemented by, for example, a semiconductor memory element such as a random access memory (RAM) or a flash memory, or a storage device such as a hard disk or an optical disk.

The chemical structural formula file 140a is a file including information of the rational formula (chemical structural formula) of the high-molecular compound. FIG. 5 is a table illustrating an example of a data structure of the chemical structural formula file. As illustrated in FIG. 5, this chemical structural formula file 140a associates compound identification information with the rational formula. The compound identification information is information that uniquely identifies the high-molecular compound. The rational formula is sequence information indicating the rational formula (chemical structural formula) of the high-molecular compound. For example, the high-molecular compound corresponds to starch, glycogen, cellulose, amylopectin, or the like, but is not limited thereto, and may be another high-molecular compound.

The branch code table 140b is a table that defines a code assigned to the branch symbol. FIG. 6 is a table illustrating an example of a data structure of the branch code table. As illustrated in FIG. 6, this branch code table 140b associates the branch symbol with the compression code. The branch symbol is a symbol representing the branched portion of the high-molecular compound. The compression code is a compression code assigned to the branch symbol. The "h" in the compression code represents hexadecimal.

The group dictionary 140c is dictionary information indicating the relationship between the sequence of the rational formula of the compound and the compression code. FIG. 7 is a table illustrating an example of a data structure of the group dictionary. As illustrated in FIG. 7, this group dictionary 140c associates the compression code, a name, grouping, and the rational formula. The compression code indicates a compression code assigned to the rational formula of a corresponding group (or functional group). The name is an example of a corresponding name. The grouping indicates grouping to which the corresponding group belongs. A name example is an example of the name of the corresponding group. The rational formula indicates a sequence that is the rational formula of the corresponding group.

Furthermore, although not illustrated in FIG. 7, the group dictionary 140c retains information that defines the relationship between the unit character string and the compression code described in FIGS. 1 to 3 and the like.

The group hidden Markov model (HMM) 140*d* is information that associates a certain group with another group that is highly likely to co-occur in the sequence of the high-molecular compound. In the following description, the certain group will be referred to as a "first group" and the another group that co-occurs with the first group will be referred to as a "second group" as appropriate.

FIG. 8 is a table illustrating an example of a data structure of a group HMM. As illustrated in FIG. 8, this group HMM 140*d* associates the compression code, the name example, the grouping, and a co-occurrence rate of the group. The compression code indicates a compression code assigned to the rational formula of the first group. The name example is an example of the name of the corresponding first group. The grouping indicates grouping to which the corresponding first group belongs.

In the co-occurrence rate of the group, for the second group co-occurring with the first group, the compression code of the second group and the co-occurrence rate are given. For example, to describe the first row, in the high-molecular compound, the second groups co-occurring with the first group (compression code: 8000h) are a group with the compression code "8028h", a group with the compression code "8132h", a group with the compression code "80F5h", and the like. Furthermore, the co-occurrence rate of the first group "compression code: 8000h" and the second group "compression code: 8028h" is "78%". The co-occurrence rate of the first group "compression code: 8000h" and the second group "compression code: 8132h" is "63%". The co-occurrence rate of the first group "compression code: 8000h" and the second group "compression code: 80F5h" is "33%".

The chemical structural formula compressed file 140*e* is a file including information of the encoded rational formula (chemical structural formula) of the high-molecular compound. FIG. 9 is a table illustrating an example of a data structure of the chemical structural formula compressed file. As illustrated in FIG. 9, this chemical structural formula compressed file 140*e* associates the compound identification information and the compression code sequence. The compound identification information is information that uniquely identifies the high-molecular compound. The compression code sequence is information obtained by encoding the rational formula in units of the unit character string.

Figure 10:
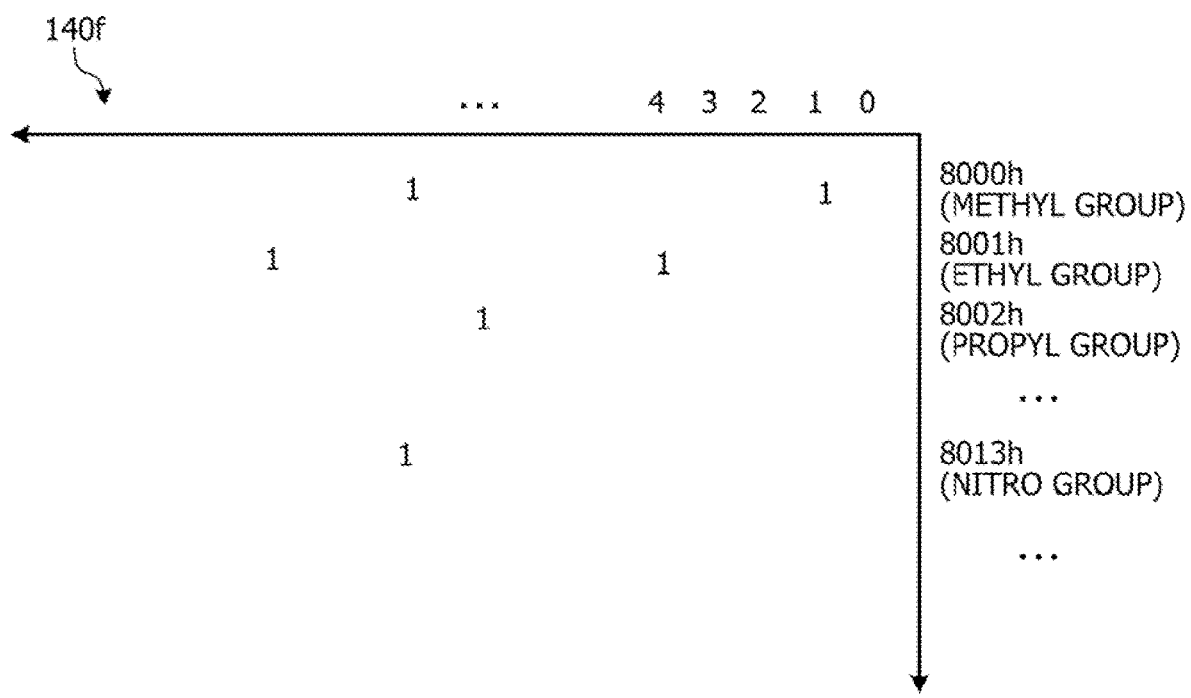
FIG. 10 is a diagram illustrating an example of a data structure of a first transposed index.

The first transposed index 140*f* is index information indicating a relationship between the compression code of the unit character string or the branch symbol included in the chemical structural formula compressed file 140*e* and an appearance position of the compression code. FIG. 10 is a diagram illustrating an example of a data structure of the first transposed index. As illustrated in FIG. 10, the first transposed index 140*f* has an offset on the horizontal axis and the compression code on the vertical axis. The offset indicates the appearance position from the lead compression code of the chemical structural formula compressed file 140*e* to the corresponding compression code. The offset of the lead compression code is set to "0".

The first transposed index 140*f* may define a relationship between the compression code and the offset for the compression code sequence for each piece of compound identification information illustrated in FIG. 9. For example, a transposed index of the compression code sequence of the compound identification information "C101" and a transposed index of the compression code sequence of the compound identification information "C102" may be defined.

The group primary structure dictionary 140*g* is dictionary information indicating a relationship between the compression code sequence (a plurality of successive compression codes) of the rational formula of the high-molecular compound and the compression code of one group primary structure. The group primary structure indicates a structure in which a plurality of groups is combined.

FIG. 11 is a table illustrating an example of a data structure of the group primary structure dictionary. As illustrated in FIG. 11, this group primary structure dictionary 140*g* associates the compression code, the grouping, the name, and the compression code sequence. The compression code is a compression code corresponding to the group primary structure. The grouping indicates grouping to which the corresponding group primary structure belongs. The name is an example of the name of the group primary structure. The compression code sequence is a sequence of the compression codes corresponding to a plurality of groups contained in the group primary structure, and the compression codes of groups correspond to the compression codes of groups defined in the group dictionary 140*c*.

The group primary structure HMM 140*h* is information that associates a certain group primary structure with another group primary structure that is highly likely to co-occur in the sequence of the high-molecular compound. In the following description, the certain group primary structure will be referred to as a "first group primary structure", and the another group primary structure co-occurring with the first group primary structure will be referred to as a "second group primary structure".

FIG. 12 is a table illustrating an example of a data structure of the group primary structure HMM. As illustrated in FIG. 12, this group primary structure HMM 140*h* associates the compression code, the grouping, the name, and the co-occurrence rate of the group primary structure. The compression code indicates a compression code assigned to the first group primary structure. The grouping indicates grouping to which the corresponding first group primary structure belongs. The name is an example of the name of the corresponding first group primary structure.

The co-occurrence rate of the group primary structure indicates the compression code of the second group primary structure and the co-occurrence rate for the second group primary structure co-occurring with the first group primary structure. For example, to describe the first row, the compression codes of the second group primary structure co-occurring with the first group primary structure (compression code: F00000h) are "F00011h", "F00101h", and "F00225h" in the high-molecular compound.

Furthermore, the co-occurrence rate of the first group primary structure "compression code: F00000h" and the second group "compression code: F00011h" is "78%". The co-occurrence rate of the first group primary structure "compression code: F00000h" and the second group "compression code: F00101h" is "63%". The co-occurrence rate of the first group primary structure "compression code: F00000h" and the second group "compression code: F00225h" is "51%".

The group primary structure compressed file 140*i* is a file including information of the rational formula of the high-molecular compound encoded in units of the group primary structure. FIG. 13 is a table illustrating an example of a data structure of the group primary structure compressed file. As illustrated in FIG. 13, this group primary structure compressed file 140i associates the compound identification information with the compression code sequence of the group primary structure. The compound identification information is information that uniquely identifies the high-molecular compound. The compression code sequence is information obtained by encoding the rational formula in units of the group primary structure.

Figure 14:
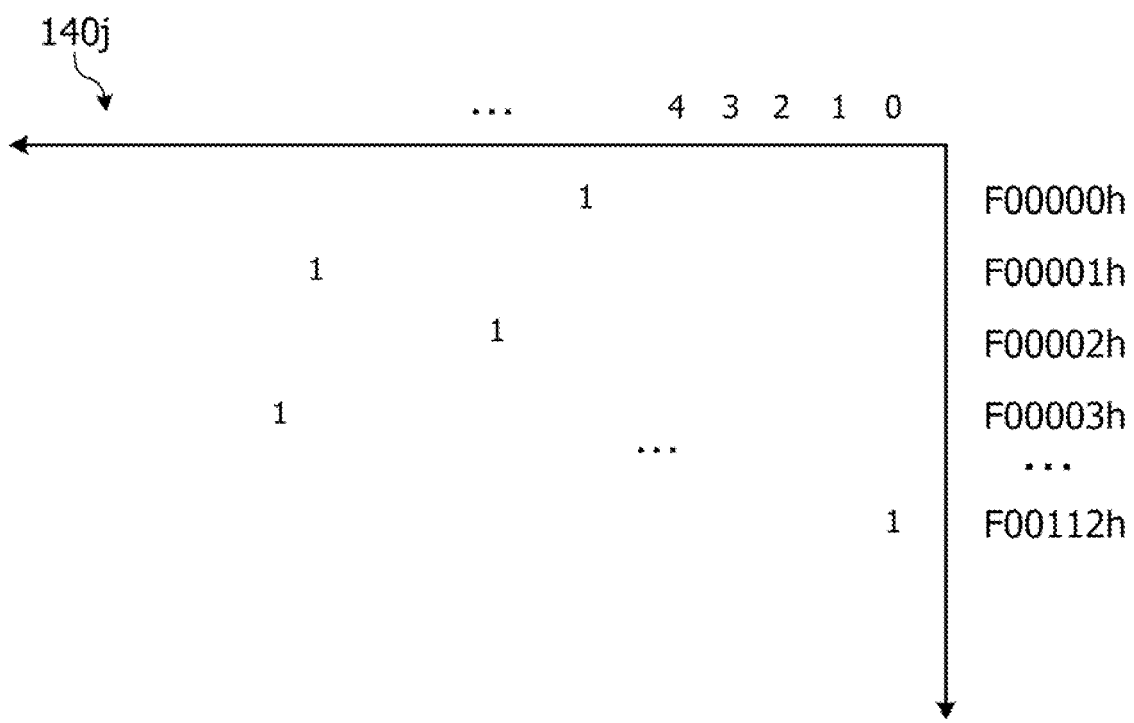
FIG. 14 is a diagram illustrating an example of a data structure of a second transposed index.

The second transposed index 140j is index information indicating a relationship between the compression code of the group primary structure included in the group primary structure compressed file 140i and the appearance position of the compression code. FIG. 14 is a diagram illustrating an example of a data structure of the second transposed index. As illustrated in FIG. 14, the second transposed index 140j has an offset on the horizontal axis and the compression code on the vertical axis. The offset indicates the appearance position from the lead compression code of the group primary structure compressed file 140i (the compression code in units of the group primary structure) to the corresponding compression code. The offset of the lead compression code is set to "0".

The second transposed index 140j may define the relationship between the compression code and the offset for the compression code sequence for each piece of compound identification information illustrated in FIG. 13. For example, a transposed index of the compression code sequence of the compound identification information "C101" and a transposed index of the compression code sequence of the compound identification information "C102" may be defined.

The property management table 140k is a table that defines groups having similar properties. FIG. 15 is a table illustrating an example of a data structure of the property management table. As illustrated in FIG. 15, this property management table 140k associates a property number, the compression code, and the name. The property number is a number that identifies the property of the group primary structure, and the same property number is assigned to the compression codes of groups having similar properties. The compression code is the compression code of the group. The name is the name of the group.

In the example illustrated in FIG. 15, the same property code "I102" is assigned to the compression code "8004h", the compression code "8005h", the compression code "8006h", and the compression code "8007h". Therefore, it means that the groups corresponding to the compression code "8004h", the compression code "8005h", the compression code "8006h", and the compression code "8007h" have similar properties.

Although not described in FIG. 15, the property management table 140k may retain information in which the property number is associated with the compression codes of the groups having similar properties.

The group vector table 140l is a table that retains a vector of the compression code assigned to each group included in the high-molecular compound. FIG. 16A is a table illustrating an example of a data structure of the group vector table. As illustrated in FIG. 16A, the group vector table 140l associates the compression code of the group with the vector. Note that the group vector table 140l may retain a vector corresponding to the branch symbol defined in the branch code table 140b.

The group primary structure vector table 140m is a table that retains the vector of the compression code assigned to each group primary structure included in the high-molecular compound. FIG. 16B is a table illustrating an example of a data structure of the group primary structure vector table. As illustrated in FIG. 16B, the group primary structure vector table 140m associates the compression code of the group primary structure with the vector.

The transition table 140n is a table that retains information of the vector of the high-molecular compound. FIG. 16C is a table illustrating an example of a data structure of the transition table. As illustrated in FIG. 16C, the transition table 140n has the compound identification information and a plurality of vectors. The compound identification information is information that uniquely identifies the high-molecular compound. The plurality of vectors represents the vectors of the group primary structures contained in the high-molecular compound. For example, a vector (n) is a vector of the group primary structure located in the n-th position from the lead of the high-molecular compound.

The description returns to FIG. 4. The control unit 150 includes an acquisition unit 151, a first encoding unit 152, a second encoding unit 153, a vector calculation unit 154, and a similarity evaluation unit 155. The control unit 150 is implemented by, for example, a central processing unit (CPU) or a micro processing unit (MPU). Furthermore, the control unit 150 may be executed by, for example, an integrated circuit such as an application specific integrated circuit (ASIC) or a field programmable gate array (FPGA).

The acquisition unit 151 is a processing unit that acquires various types of information from an external device or the like via a network. For example, the acquisition unit 151 acquires the chemical structural formula file 140a and stores the acquired chemical structural formula file 140a in the storage unit 140. The acquisition unit 151 may acquire the group dictionary 140c, the group HMM 140d, the group primary structure dictionary 140g, and the group primary structure HMM 140h, and store the acquired information in the storage unit 140.

The first encoding unit 152 is a processing unit that acquires the rational formula of the high-molecular compound from the chemical structural formula file 140a and encodes the acquired rational formula. Hereinafter, an example of the processing of the first encoding unit 152 will be described.

The first encoding unit 152 divides the sequence included in the rational formula into the unit character string or the branch symbol by executing the morphological analysis for the rational formula of the high-molecular compound. The processing in which the first encoding unit 152 executes the morphological analysis to divide the sequence into the unit character string or the branch symbol corresponds to the processing described in FIGS. 1, 2, and 3.

In a case where there is a plurality of unit character strings to be division candidates, the first encoding unit 152 may perform division by selecting the unit character string having a higher co-occurrence rate on the basis of the group HMM 140d.

The first encoding unit 152 generates the compression code sequence by encoding the rational formula using the branch code table 140b and the group dictionary 140c after dividing the rational formula of the high-molecular compound into the unit character string or the branch symbol. The compression code sequence generated by the first encoding unit 152 corresponds to a "first coded sequence". The first encoding unit 152 associates and registers the compound identification information and the compression code sequence in the chemical structural formula compressed file 140e.

The first encoding unit 152 registers the relationship between the type of the compression code and the offset in the first transposed index 140f in a case of assigning the compression code to the unit character string or the branch symbol of the rational formula of the high-molecular compound. For example, in a case where the offset of the compression code "8000h" is "1" in the compression code sequence (first coded sequence) of the rational formula of the high-molecular compound, the first encoding unit 152 sets "1" at an intersection portion of a column of the offset "1" of the first transposed index 140f and a row of the compression code "8000h".

The first encoding unit 152 generates the chemical structural formula compressed file 140e by acquiring the information of the rational formula corresponding to unselected compound identification information from the chemical structural formula file 140a and repeatedly executing the above-described processing.

The second encoding unit 153 is a processing unit that acquires the compression code sequence (first coded sequence) of the high-molecular compound from the chemical structural formula compressed file 140e, and encodes the acquired compression code sequence in units of the group primary structure. The relationship between the compression code sequence of the high-molecular compound and the compression code of the group primary structure is defined in the group primary structure dictionary 140g.

Figure 17:
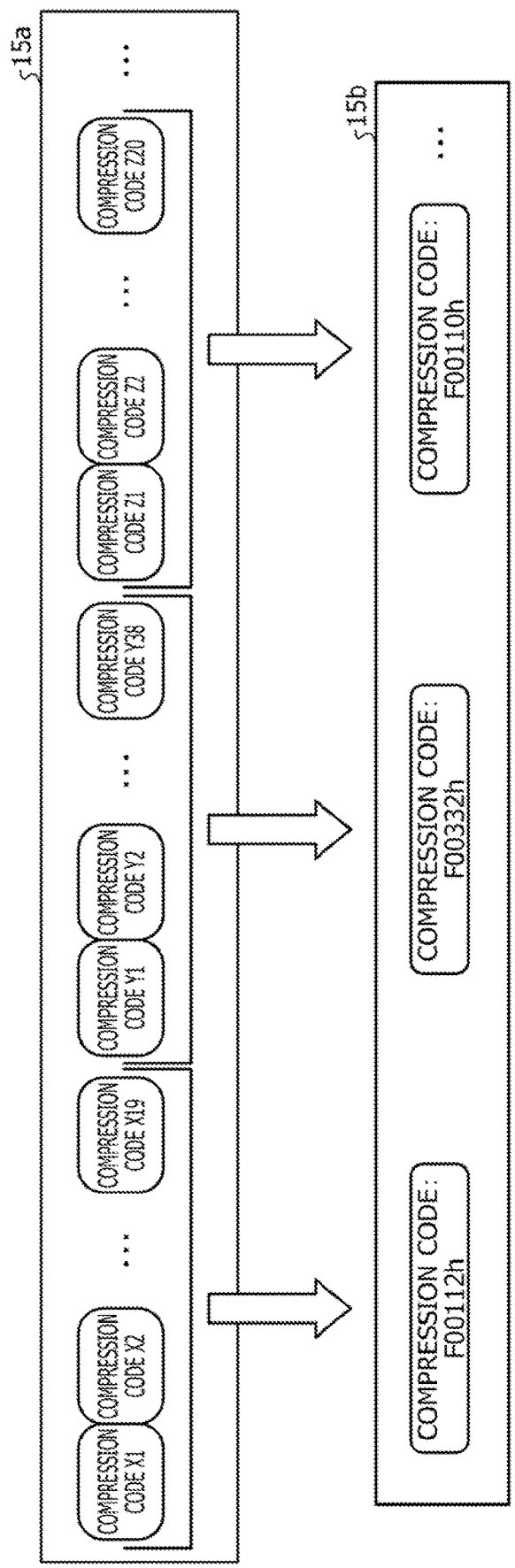
FIG. 17 is a diagram for describing processing of a second encoding unit.

FIG. 17 is a diagram for describing processing of the second encoding unit. In FIG. 17, a compression code sequence 15 is assumed to be a compression code sequence 15a corresponding to the compound identification information "C101" registered in the chemical structural formula compressed file 140e. Each compression code included in the compression code sequence 15a is the compression code of the unit code or the compression code of the branch symbol defined in the group dictionary 140c.

For example, in the group primary structure dictionary 140g, it is assumed that the compression codes X1, X2, . . . , and X19 of the compression code sequence 15a are associated with the compression code "F00112h" of the group primary structure. In this case, the second encoding unit 153 assigns the compression code "F00112h" of the group primary structure to each of the compression codes X1, X2, . . . , and X19.

In the group primary structure dictionary 140g, it is assumed that the compression codes Y1, Y2, . . . , and Y38 of the compression code sequence 15a are associated with the compression code "F00332h" of the group primary structure. In this case, the second encoding unit 153 assigns the compression code "F00332h" of the group primary structure to each of the compression codes Y1, Y2, . . . , and Y38.

In the group primary structure dictionary 140g, it is assumed that the compression codes Z1, Z2, . . . , and Z20 of the compression code sequence 15a are associated with the compression code "F00110h" of the group primary structure. In this case, the second encoding unit 153 assigns the compression code "F00110h" of the group primary structure to each of the compression codes Z1, Z2, . . . , and Z20.

The second encoding unit 153 generates a compression code sequence 15b obtained by encoding the compression code sequence 15a in units of the group primary structure by repeatedly executing the above-described processing on the basis of the group primary structure dictionary 140g. The compression code sequence 15b corresponds to a "second coded sequence".

The second encoding unit 153 associates and registers the compound identification information and the compression code sequence in the group primary structure compressed file 140i.

In the process of comparing the compression code sequence 15a with the group primary structure dictionary 140g and performing encoding, in a case where a plurality of compression codes in units of the group primary structure becomes candidates for encoding, the second encoding unit 153 may select and assign a compression code with a higher co-occurrence rate on the basis of the group primary structure HMM 140h.

The second encoding unit 153 registers the relationship between the type of the compression code and the offset in the second transposed index 140j in a case of encoding in units of the group primary structure. For example, in the compression code sequence (second coded sequence) of the rational formula of the high-molecular compound, the offset of the compression code "F00112h" is "0". In this case, the second encoding unit 153 sets "1" at the intersection portion of the column of the offset "0" of the first transposed index 140f and the row of the compression code "F00112h".

The second encoding unit 153 generates the group primary structure compressed file 140i by acquiring the compression code sequence of the rational formula corresponding to unselected compound identification information from the chemical structural formula compressed file 140e, and repeatedly executing the above-described processing.

Furthermore, the second encoding unit 153 outputs the relationship among the compression code of the group primary structure, the compression codes of the plurality of groups corresponding to the compression code of the group primary structure, and the compression code of the branch symbol to the vector calculation unit 154.

The description returns to FIG. 4. The vector calculation unit 154 is a processing unit that acquires the compression code sequence (second coded sequence) of the high-molecular compound from the group primary structure compressed file 140i and calculates the vector of the high-molecular compound. The vector calculation unit 154 acquires the compression code of the group primary structure from the group primary structure compressed file 140i, and calculates the vector of the acquired compression code by executing the following processing. The vector calculation unit 154 acquires, from the above-described second encoding unit 153, the relationship among the compression code of the group primary structure, the compression codes of the plurality of groups, and the compression code of the branch symbol.

The vector calculation unit 154 calculates each vector corresponding to the compression code by embedding the compression code for each group in a vector space such as a Poincare space. The vector calculation unit 154 may also calculate a vector of the compression code of the branch symbol by embedding the compression code in the Poincare space, or may assign the vector in advance. The vector calculation unit 154 associates and registers the compression code of the group with the vector in the group vector table 140l.

The vector calculation unit 154 calculates the vector of the group primary structure by adding the vectors assigned to the compression code of each group and the compression code of the branch symbol included in the group primary structure. The vector calculation unit 154 associates and registers the compression code of the group primary structure with the vector in the group primary structure vector table 140m.

The high-molecular compound contains a plurality of group primary structures. The vector calculation unit 154 associates and registers the compound identification information with the vector for each group primary structure in the transition table 140n. The vector calculation unit 154 registers the vectors of the group primary structures in the transition table 140n in the order in which the group primary structures appear.

Here, the processing in which the vector calculation unit 154 embeds the compression code of the group in the Poincare space to calculate the vector is a technique called Poincare embeddings. For Poincare embeddings, for example, the technique described in non-patent document "Valentin Khrulkov et al. "Hyperbolic Image Embeddings" Cornell University, 2019 Apr. 3", or the like may be used.

In Poincare embeddings, a vector is assigned according to an embedded position in the Poincare space, and the more similar information is, the closer the information is embedded. The vector calculation unit 154 specifies the compression codes for the groups having similar properties on the basis of the property management table 140k.

Figure 18:
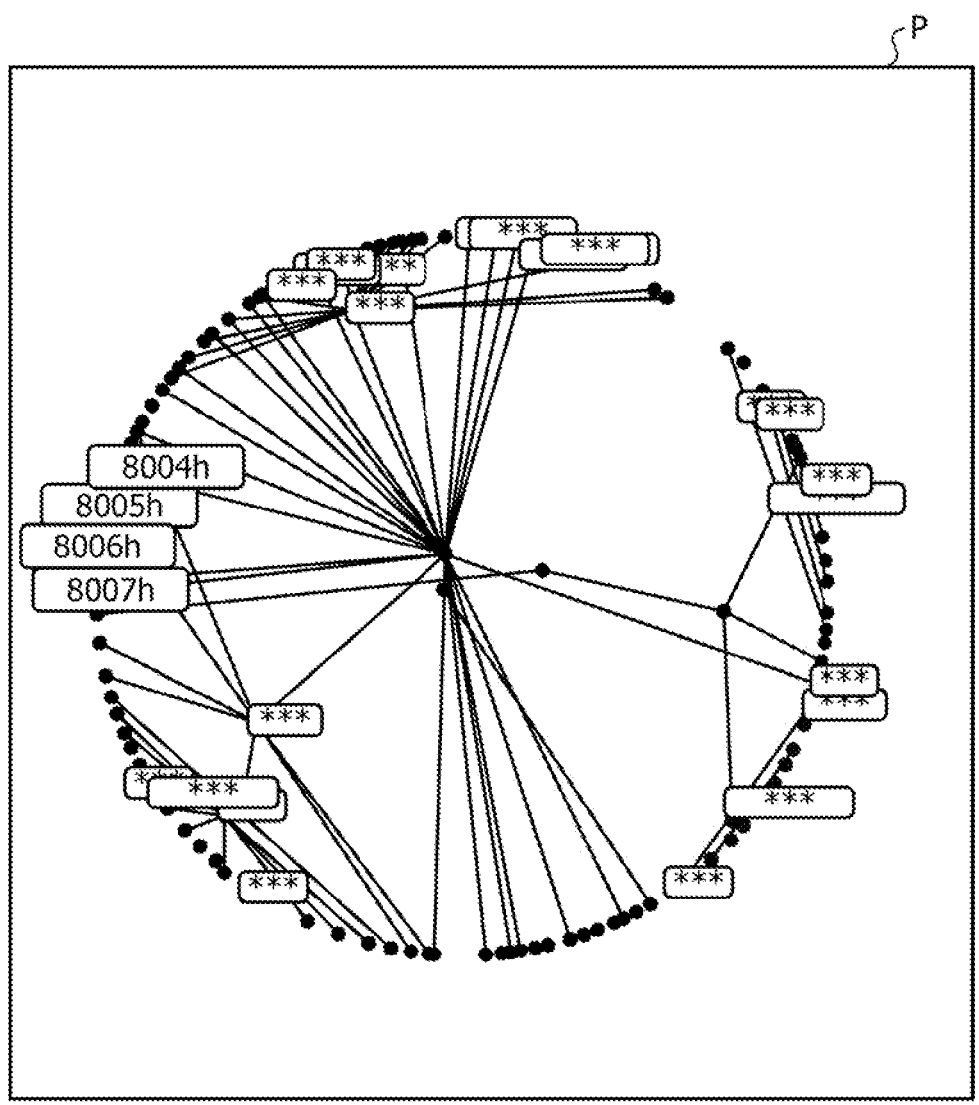
FIG. 18 is a diagram illustrating an example of a Poincare space.

FIG. 18 is a diagram illustrating an example of the Poincare space. As described in FIG. 15, the groups corresponding to the compression code "8004h", the compression code "8005h", the compression code "8006h", and the compression code "8007h" have similar properties. Therefore, the vector calculation unit 154 embeds the compression code "8004h", the compression code "8005h", the compression code "8006h", and the compression code "8007h" at positions close to each other in a Poincare space P, and provides vectors according to the positions.

The vector calculation unit 154 calculates the vector of the compression code of each group primary structure contained in the compression code sequence of the high-molecular compound in order from the top, and registers the vector in the transition table 140n in order. The vector calculation unit 154 generates the transition table 140n by acquiring the compression code sequence of the rational formula corresponding to unselected compound identification information from the group primary structure compressed file 140i, and repeatedly executing the above-described processing.

The similarity evaluation unit 155 is a processing unit that evaluates the similarity of high-molecular compounds by comparing the vectors corresponding to the pieces of compound identification information registered in the transition table 140n. For example, the similarity evaluation unit 155 calculates a vector distance of the high-molecular compounds, and specifies a set of the high-molecular compounds with the distance that is less than a threshold as mutually similar high-molecular compounds.

For example, the similarity evaluation unit 155 may calculate the vector distance of the high-molecular compounds, using vectors obtained by accumulating vectors of the group primary structures corresponding to the high-molecular compounds registered in the transition table 140n as the vectors of the high-molecular compounds. The similarity evaluation unit 155 may output an evaluation result to the display unit 130 for display, or may notify an external device or the like.

Figure 19:
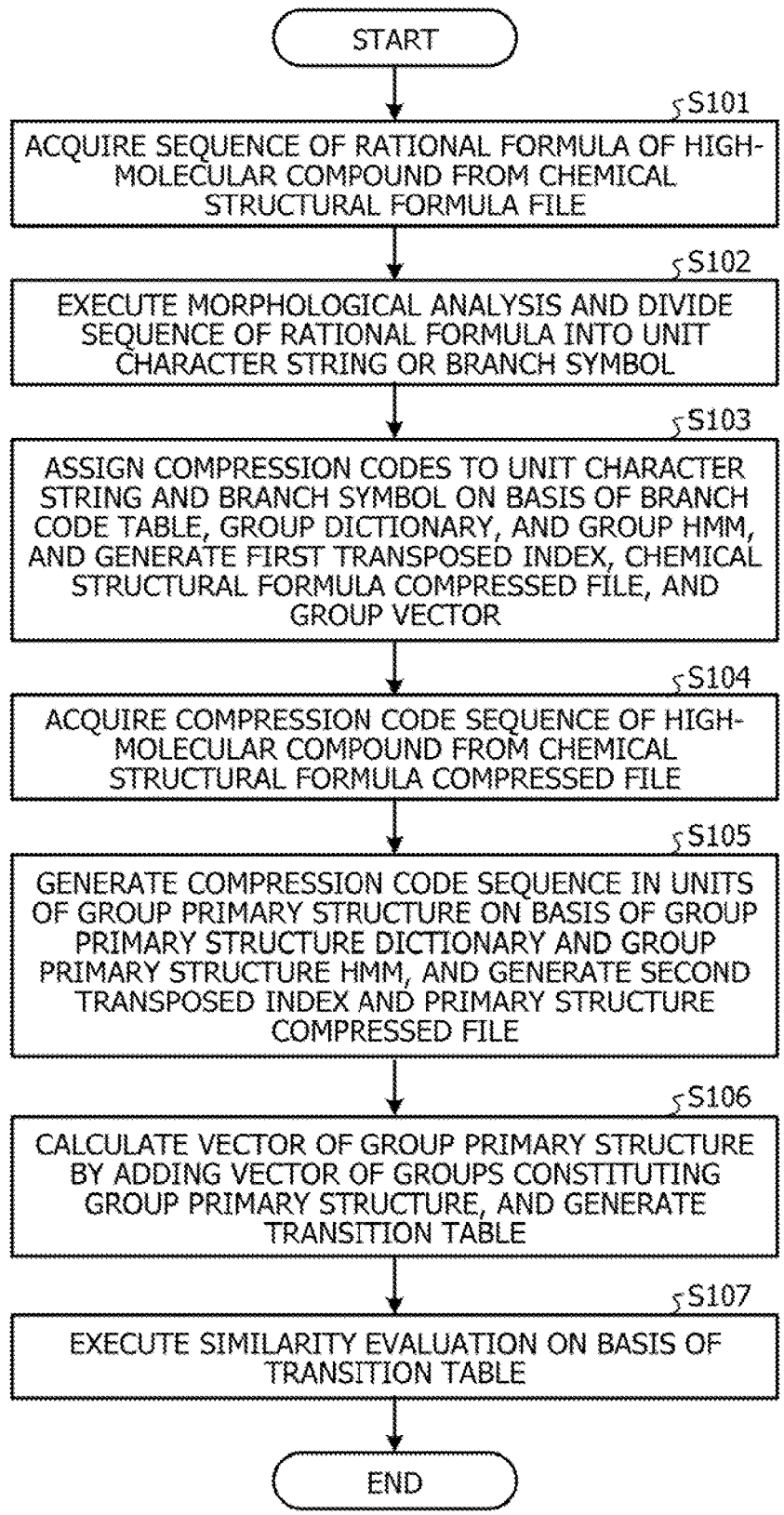
FIG. 19 is a flowchart illustrating a processing procedure of the information processing device according to the present embodiment.

Next, an example of a processing procedure of the information processing device 100 according to the present embodiment will be described. FIG. 19 is a flowchart illustrating a processing procedure of the information 19, the first encoding unit 152 of the information processing device 100 acquires the sequence of the rational formula of the high-molecular compound from the chemical structural formula file 140a (step S101).

The first encoding unit 152 executes the morphological analysis and divides the sequence of the rational formula into the unit character string or the branch symbol (step S102). The first encoding unit 152 assigns the compression code to the unit character string or the branch symbol on the basis of the branch code table 140b, the group dictionary 140c, and the group HMM 140d, and generates the first transposed index 140f and the chemical structural formula compressed file 140e. Furthermore, the vector calculation unit 154 of the information processing device 100 generates the vector of the group by embedding the group in the Poincare space (step S103).

The second encoding unit 153 of the information processing device 100 acquires the compression code sequence of the high-molecular compound from the chemical structural formula compressed file 140e (step S104). The second encoding unit 153 generates the compression code sequence in units of the group primary structure on the basis of the group primary structure dictionary 140g and the group primary structure HMM 140h, and generates the second transposed index 140j and the group primary structure compressed file 140i (step S105).

The vector calculation unit 154 of the information processing device 100 calculates the vector of the group primary structure by adding the vectors of the groups constituting the units of the group primary structure stored in the group primary structure compressed file 140i, and generates the transition table 140n (step S106). The similarity evaluation unit 155 of the information processing device 100 executes similarity evaluation on the basis of the transition table 140n (step S107).

Next, effects of the information processing device 100 according to the present embodiment will be described. The information processing device 100 divides the rational formula of the high-molecular compound into the unit character string and the branch symbol and assigns the compression code to generate the compression code sequence, and moreover converts the compression code sequence to each compression code of each group primary structure. The information processing device collectively embeds the groups having similar properties into the Poincare space on the basis of the compression code for each group to generate the group vector for appropriately expressing the property of the compound. By executing the similarity evaluation using the vector generated by the processing of the information processing device 100, the accuracy of the similarity evaluation can be improved.

The information processing device 100 adds the vectors of the groups to calculate the vector of the group primary structure, using the compression codes constituting the group primary structure, and generates the transition table. Therefore, a highly accurate vector can be assigned to the group primary structures having similar properties.

The information processing device 100 can accurately evaluate the high-molecular compounds having similar properties by comparing the vectors of the group primary structures corresponding to the high-molecular compounds stored in the transition table 140n.

By the way, the above-described processing of the information processing device 100 according to the present embodiment is an example, and another processing may be executed. As described with reference to FIGS. 1 to 3, the information processing device 100 assigns the compression codes according to granularity of the unit character strings and branch symbols included in the group when encoding the rational formula of the high-molecular compound, but the embodiment is not limited to the case.

Figure 20:
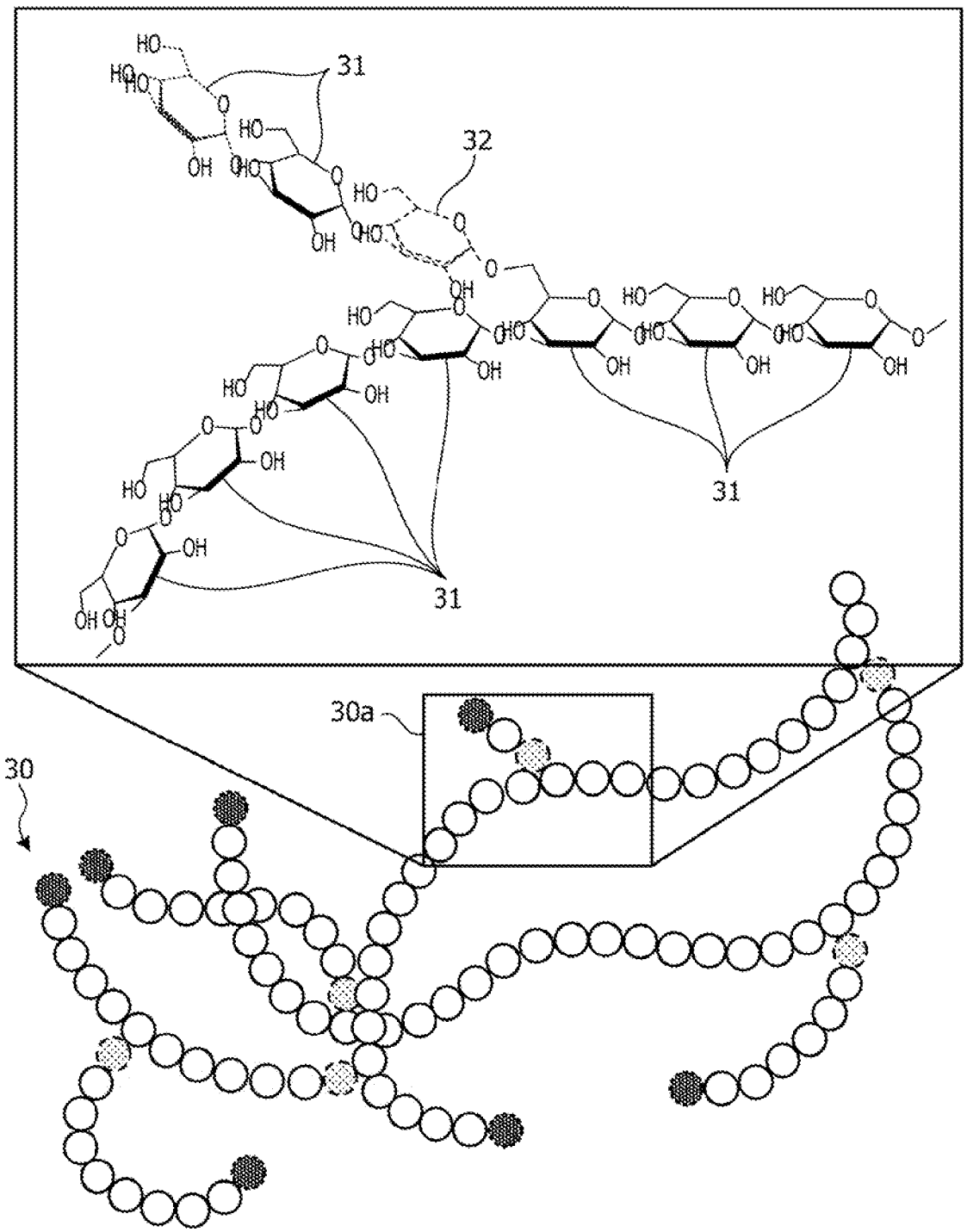
FIG. 20 is a diagram for describing another processing of the information processing device according to the present embodiment.

The information processing device 100 may perform encoding by regarding a group as the minimum unit and assigning the compression code specific to a branching group to the group located at the branched portion. FIG. 20 is a diagram for describing another processing of the information processing device according to the present embodiment. In FIG. 20, glycogen is used as an example of the high-molecular compound.

A high-molecular compound 30 illustrated in FIG. 20 is configured by connecting a plurality of groups. A description will be given focusing on a region 30a of the high-molecular compound 30. The region 30a includes a plurality of groups 31 and a group 32 of the branched portion. The first encoding unit 152 of the information processing device 100 assigns the compression codes to the plurality of groups 31 on the basis of the group dictionary 140c. Furthermore, the first encoding unit 152 assigns the compression code specific to the branched portion to the group 32 of the branched portion.

Figure 21:
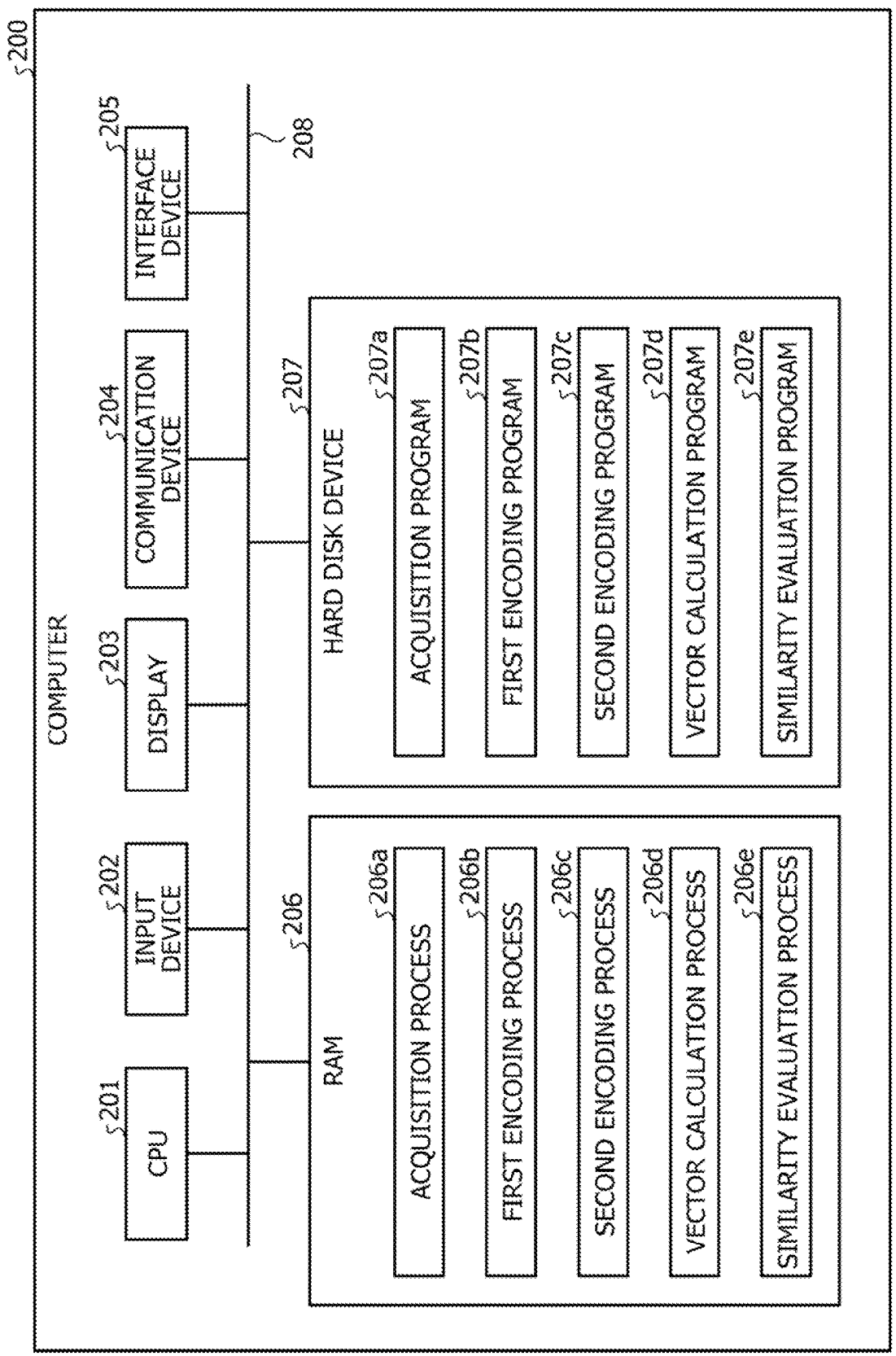
FIG. 21 is a diagram illustrating an example of a hardware configuration of a computer that implements functions similar to those of the information processing device according to the embodiment.

Next, an exemplary hardware configuration of a computer that implements functions similar to those of the information processing device 100 described in the embodiment above will be described. FIG. 21 is a diagram illustrating an example of a hardware configuration of a computer that implements functions similar to those of the information processing device according to the embodiment.

As illustrated in FIG. 21, a computer 200 includes a CPU 201 that executes various types of arithmetic processing, an input device 202 that receives data input from a user, and a display 203. Furthermore, the computer 200 includes a communication device 204 that exchanges data with an external device or the like via a wired or wireless network, and an interface device 205. Furthermore, the computer 200 includes a RAM 206 that temporarily stores various types of information, and a hard disk device 207. Then, each of the devices 201 to 207 is connected to a bus 208.

The hard disk device 207 has an acquisition program 207a, a first encoding program 207b, a second encoding program 207c, a vector calculation program 207d, and a similarity evaluation program 207e. Furthermore, the CPU 201 reads each of the programs 207a to 207e, and loads the read program to the RAM 206.

The acquisition program 207a functions as an acquisition process 206a. The first encoding program 207b functions as a first encoding process 206b. The second encoding program 207c functions as a second encoding process 206c. The vector calculation program 207d functions as a vector calculation process 206d. The similarity evaluation program 207e functions as a similarity evaluation process 206e.

Processing of the acquisition process 206a corresponds to the processing of the acquisition unit 151. Processing of the first encoding process 206b corresponds to the processing of the first encoding unit 152. Processing of the second encoding process 206c corresponds to the processing of the second encoding unit 153. Processing of the vector calculation process 206d corresponds to the processing of the vector calculation unit 154. Processing of the similarity evaluation process 206e corresponds to the processing of the similarity evaluation unit 155.

Note that each of the programs 207a to 207e does not necessarily have to be stored in the hard disk device 307 from the beginning. For example, each of the programs may be stored in a "portable physical medium" to be inserted in the computer 200, such as a flexible disk (FD), a compact disc read only memory (CD-ROM), a digital versatile disc (DVD), a magneto-optical disk, or an IC card. Then, the computer 200 may read and execute each of the programs 207a to 207e.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium storing an information processing program for causing a computer to perform processing comprising:
dividing a sequence that indicates a rational formula of a compound, into a character string of a minimum unit of the sequence and a branch symbol that indicates a branched portion of the compound;
generating a first coded sequence by using a group dictionary that indicates a relationship between the sequence of the rational formula of the compound and the compression code, the generating of the first coded sequence including assigning, based on the group dictionary, a compression code to the character string of the minimum unit, and assigning, based on the group dictionary, the compression code according to a type of the branched portion to the branch symbol; and
generating a second coded sequence by using a group primary structure dictionary that indicates a relationship between a group primary structure of the sequence of the rational formula of the compound and the compression code, the generating of the second coded sequence including encoding, based on the group primary structure dictionary, the compression code included in the first coded sequence in units of the group primary structure.

2. The non-transitory computer-readable storage medium according to claim 1, the processing further comprising performing vector calculation processing including
generating a group vector by embedding the compression code for each group included in the first coded sequence in a Poincare space, and
assigning the vector to the group primary structure by adding the group vector that constitutes the group primary structure.

3. The non-transitory computer-readable storage medium according to claim 2, wherein the vector calculation processing further including
embedding compression codes of groups that have a similar property to similar positions in the Poincare space to assign the compression codes to compression codes in which vectors according to positions in the Poincare space are embedded.

4. The non-transitory computer-readable storage medium according to claim 2, wherein the vector calculation processing further including
executing processing of sequentially registering, in a transition table, the vectors of a plurality of group primary structures included in the second coded sequence.

5. The non-transitory computer-readable storage medium according to claim 4, the processing further comprising
performing similarity evaluation processing including evaluating similarity of each compound on a basis of the vectors registered in the transition table.

6. An information processing method implemented by a computer, the information processing method comprising:
dividing a sequence that indicates a rational formula of a compound, into a character string of a minimum unit of the sequence and a branch symbol that indicates a branched portion of the compound;
generating a first coded sequence by using a group dictionary that indicates a relationship between the sequence of the rational formula of the compound and the compression code, the generating of the first coded sequence including assigning, based on the group dictionary, a compression code to the character string of the minimum unit, and assigning, based on the group dictionary, the compression code according to a type of the branched portion to the branch symbol; and
generating a second coded sequence by using a group primary structure dictionary that indicates a relationship between a group primary structure of the sequence of the rational formula of the compound and the compression code, the generating of the second coded sequence including encoding, based on the group primary structure dictionary, the compression code included in the first coded sequence in units of the group primary structure.

7. The information processing method according to claim 6, the processing further comprising
performing vector calculation processing including
generating a group vector by embedding the compression code for each group included in the first coded sequence in a Poincare space, and
assigning the vector to the group primary structure by adding the group vector that constitutes the group primary structure.

8. The information processing method according to claim 7, wherein the vector calculation processing further including
embedding compression codes of groups that have a similar property to similar positions in the Poincare space to assign the compression codes to compression codes in which vectors according to positions in the Poincare space are embedded.

9. The information processing method according to claim 7, wherein the vector calculation processing further including
executing processing of sequentially registering, in a transition table, the vectors of a plurality of group primary structures included in the second coded sequence.

10. The information processing method according to claim 9, the processing further comprising
performing similarity evaluation processing including evaluating similarity of each compound on a basis of the vectors registered in the transition table.

11. An information processing device comprising:
a memory; and
a processor coupled to the memory, the processor being configured to perform processing, the processing including:
dividing a sequence that indicates a rational formula of a compound, into a character string of a minimum unit of the sequence and a branch symbol that indicates a branched portion of the compound;
generating a first coded sequence by using a group dictionary that indicates a relationship between the sequence of the rational formula of the compound and the compression code, the generating of the first coded sequence including assigning, based on the group dictionary, a compression code to the character string of the minimum unit, and assigning, based on the group dictionary, the compression code according to a type of the branched portion to the branch symbol; and
generating a second coded sequence by using a group primary structure dictionary that indicates a relationship between a group primary structure of the sequence of the rational formula of the compound and the compression code, the generating of the second coded sequence including encoding, based on the group primary structure dictionary, the compression code included in the first coded sequence in units of the group primary structure.

12. The information processing device according to claim 11, the processing further comprising
performing vector calculation processing including
generating a group vector by embedding the compression code for each group included in the first coded sequence in a Poincare space, and
assigning the vector to the group primary structure by adding the group vector that constitutes the group primary structure.

13. The information processing device according to claim 12, wherein the vector calculation processing further including
embedding compression codes of groups that have a similar property to similar positions in the Poincare space to assign the compression codes to compression codes in which vectors according to positions in the Poincare space are embedded.

14. The information processing device according to claim 12, wherein the vector calculation processing further including
executing processing of sequentially registering, in a transition table, the vectors of a plurality of group primary structures included in the second coded sequence.

15. The information processing device according to claim 14, the processing further comprising
performing similarity evaluation processing including evaluating similarity of each compound on a basis of the vectors registered in the transition table.

* * * * *